(12) United States Patent
Tani et al.

(10) Patent No.: US 11,427,713 B2
(45) Date of Patent: Aug. 30, 2022

(54) FINGERPRINT DETECTION POWDER

(71) Applicant: KINSEI MATEC CO., LTD., Osaka (JP)

(72) Inventors: Kokichi Tani, Yokkaichi (JP); Junya Fujioka, Yokkaichi (JP)

(73) Assignee: KINSEI MATEC CO., LTD., Osaka (JP)

( * ) Notice: Subject to any disclaimer, the term of this patent is extended or adjusted under 35 U.S.C. 154(b) by 260 days.

(21) Appl. No.: 16/497,261

(22) PCT Filed: Dec. 27, 2017

(86) PCT No.: PCT/JP2017/047087
§ 371 (c)(1),
(2) Date: Sep. 24, 2019

(87) PCT Pub. No.: WO2018/193669
PCT Pub. Date: Oct. 25, 2018

(65) Prior Publication Data
US 2020/0385584 A1    Dec. 10, 2020

(30) Foreign Application Priority Data

Apr. 19, 2017 (JP) .............................. JP2017-083037

(51) Int. Cl.
*C09C 3/12* (2006.01)
*A61B 5/1172* (2016.01)

(52) U.S. Cl.
CPC .............. *C09C 3/12* (2013.01); *A61B 5/1172* (2013.01)

(58) Field of Classification Search
None
See application file for complete search history.

(56) References Cited

U.S. PATENT DOCUMENTS 5,262,153 A * 11/1993 Mishima ................ A61K 8/361
424/401

FOREIGN PATENT DOCUMENTS

CN    101792147 A    8/2010
CN    104352242 A    2/2015
(Continued)

OTHER PUBLICATIONS

Machine translation JP2016-06918 (Year: 2016).*
(Continued)

*Primary Examiner* — Alexandre F Ferre
(74) *Attorney, Agent, or Firm* — Oblon, McClelland, Maier & Neustadt, L.L.P.

(57) ABSTRACT

ABSTRACT A fingerprint detection powder that is capable of collecting a clear fingerprint image even from a sample with a smaller amount of fingerprint constituents adhered thereto and a sample with a smooth glassy surface. The fingerprint detection powder contains pigment particles and calcium lactate. The pigment particles preferably contain at least one selected from titanium oxide, aluminum oxide, zinc oxide, zirconium oxide, colcothar, yellow iron oxide, black iron oxide, silica, carbon black, aluminum powder, and copper powder. The surface of the pigment particles is preferably covered with the calcium lactate. The fingerprint detection powder further contains a silane coupling agent. Preferably, the silane coupling agent is n-octyltriethoxysilane. The surface of the pigment particles is preferably covered with the n-octyltriethoxysilane as well as the calcium lactate.

10 Claims, 12 Drawing Sheets

(56) References Cited

FOREIGN PATENT DOCUMENTS

| JP | 9-12439 A | | 1/1997 |
|----|-----------|---|--------|
| JP | 9-25432 A | | 1/1997 |
| JP | 2000-119135 A | | 4/2000 |
| JP | 2000119135 A | * | 4/2000 |
| JP | 2001181136 A | * | 7/2001 |
| JP | 2016-106918 A | | 6/2016 |

OTHER PUBLICATIONS

Machine translation CN104352242 (Year: 2015).*
Machine translation JP-2000119135-A (Year: 2000).*
Machine translation JP-2001181136-A (Year: 2001).*
Extended European Search Report dated Dec. 1, 2020 in corresponding European Patent Application No. 17906059.5, 7 pages
International Search Report dated Mar. 27, 2018 in PCT/JP2017/047087 filed Dec. 27, 2017.

* cited by examiner

FINGERPRINT DETECTION POWDER

TECHNICAL FIELD

The present invention relates to a fingerprint detection powder. In particular, the present invention relates to a fingerprint detection powder suitable for criminal investigations.

BACKGROUND ART

For identification, a fingerprint attached to an object must be visualized. The method for visualizing a fingerprint includes a method including applying a fine powder to a portion where the finger touches. Secretion (hereinafter referred to as "fingerprint component") is produced from the sweat gland opening of the human fingerprint ridges. The fingerprint component adheres to a portion where the finger touches. When a fine powder that easily adheres to the fingerprint component is applied to the portion, the fine powder adheres to the fingerprint component. The fine powder adheres to the fingerprint component, whereby the fingerprint is visualized. When the fine powder is transferred to gelatin paper, the visualized fingerprint is to be collected. Conventionally, for example, aluminum powder has been used as such a fine powder. However, aluminum powder is unfortunately difficult to clean from the applied portion. This is due to the strong adhesive and scattering properties of aluminum powder. Because cleaning is difficult, aluminum powder is hard to apply over a wide area. When aluminum powder is used to collect a fingerprint, it is necessary for collection to focus on a portion where the fingerprint possibly exists.

Patent Document 1 discloses a fingerprint detection powder. This fingerprint detection powder contains pigment particles and calcium lactate. The fingerprint detection powder disclosed in Patent Document 1 can suppress powder scattering and adhesion to portions other than a portion where a fingerprint exists when collecting a fingerprint, facilitate removal, and suppress influence of the collector's skill on fingerprint collection, compared to aluminum powder.

PRIOR ART DOCUMENT

Patent Document

Patent Document 1: Japanese Patent Application Laid-open No. 2016-106918

SUMMARY OF THE INVENTION

Problems to be Solved by the Invention

The fingerprint detection powder disclosed in Patent Document 1 has a problem in that a fingerprint is likely to become unclear when the fingerprint is detected from a sample with less adhesion of fingerprint component. In addition, the fingerprint detection powder disclosed in Patent Document 1 has a problem in that when a fingerprint is collected from a smooth glassy surface, the detected ridges may be scraped so that the evidence ability is impaired.

An object of the present invention is to provide a fingerprint detection powder capable of achieving collection of a clear fingerprint image even from a sample with less adhesion of fingerprint component and a sample on a smooth glassy surface.

Solutions to the Problems

In order to solve the above problems, a fingerprint detection powder of the present disclosure contains pigment particles and calcium lactate. The fingerprint detection powder is characterized by further containing a silane coupling agent.

In addition, the fingerprint detection powder is characterized in that, the silane coupling agent includes a substance represented by the following formula (1).

[Chemical Formula 1]

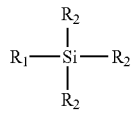

wherein $R_1$ is an alkyl group or an aryl group, and $R_2$ is an alkoxy group having 1 or 2 carbon atoms.

In addition, the fingerprint detection powder is characterized in that, $R_1$ is an alkyl group having 7 or more and 10 or less carbon atoms.

In addition, the fingerprint detection powder is characterized in that, the alkyl group having 7 or more and 10 or less carbon atoms is an octyl group.

In addition, the fingerprint detection powder is characterized in that, the weight % of the substance represented by the formula (1) in the fingerprint detection powder is 0.1 wt % or more and 20 wt % or less.

In addition, the fingerprint detection powder is characterized in that, the weight % of the substance represented by the formula (1) in the fingerprint detection powder is 0.5 wt % or more and 5 wt % or less.

In addition, the fingerprint detection powder is characterized in that, the surface of the pigment particles is covered with a silane coupling agent.

In addition, the fingerprint detection powder is characterized in that, the surface of the pigment particles is covered with calcium lactate together with the silane coupling agent.

In addition, the fingerprint detection powder is characterized in that, the calcium lactate is calcium L-lactate.

In addition, the fingerprint detection powder is characterized in that, the calcium L-lactate is hydrate.

In addition, the fingerprint detection powder is characterized in that, the pigment particles include at least one type selected from the group consisting of titanium oxide, aluminum oxide, zinc oxide, zirconium oxide, red iron oxide, yellow iron oxide, black iron oxide, silica, carbon black, aluminum powder and copper powder.

Effects of the Invention

The fingerprint detection powder of the present invention is capable of achieving collection of a clear fingerprint image even from a sample with less adhesion of fingerprint component and a sample on a smooth glassy surface.

COMPONENT OF FINGERPRINT DETECTION POWDER

Figure 1:
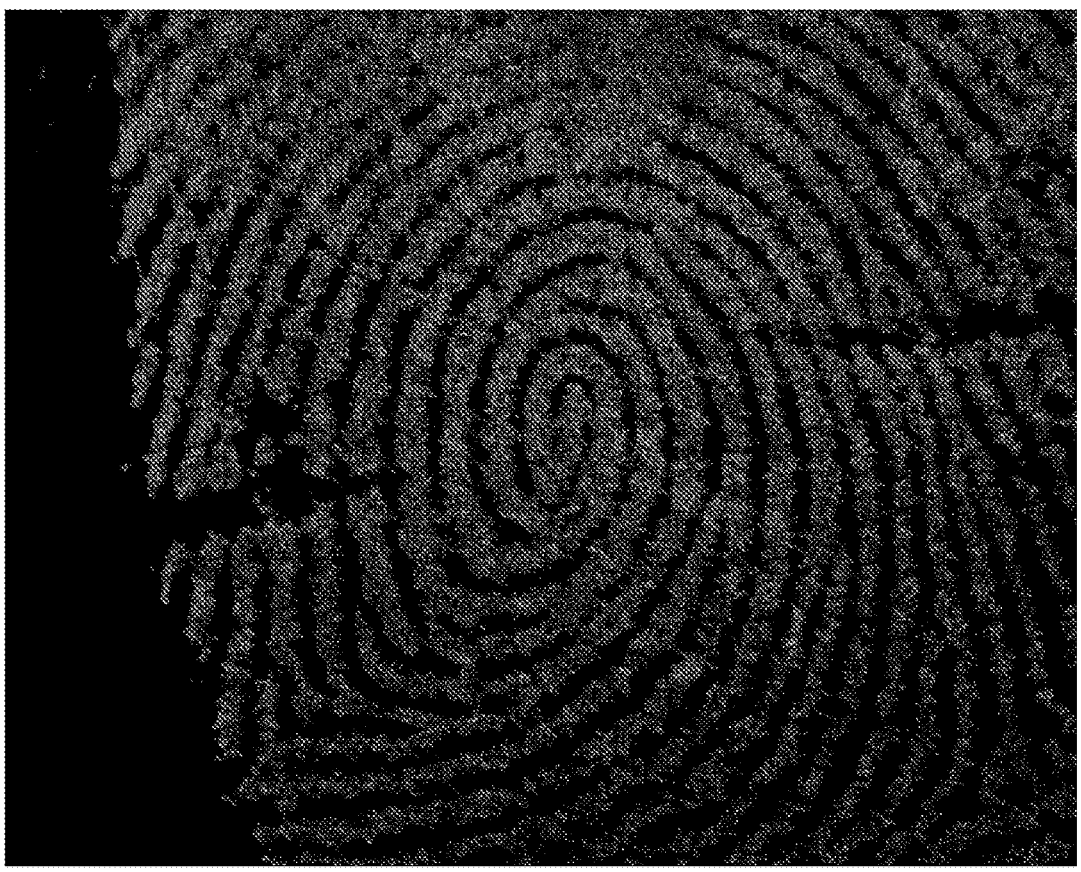
FIG. 1 is a fingerprint image when a fingerprint detection powder according to Example 1 is applied to the fingerprint No. 1 attached to an acrylic plate.

A fingerprint detection powder according to the present invention contains pigment particles (particles containing a well-known substance known as a pigment) and calcium lactate. By containing calcium lactate, the fingerprint detection powder according to the present invention can reduce adhesion of the fingerprint detection powder to portions other than the fingerprint component. The reason why adhesion of the fingerprint detection powder to portions other than the fingerprint component can be reduced is because the affinity of the fingerprint component for the pigment particles can increase. Because adhesion of the fingerprint detection powder to portions other than the fingerprint component can be reduced, the possibility that a fingerprint image remains disappeared even when the fingerprint detection powder is applied is suppressed. The fingerprint detection powder according to the present invention is characterized by further containing a silane coupling agent in addition to the pigment particles and calcium lactate. The silane coupling agent referred to in the present invention is an organosilicon compound capable of binding an organic material to an inorganic material. The fingerprint detection powder according to the present invention contains a silane coupling agent, whereby the pigment particles adhere more firmly to the fingerprint component, compared to a case of containing no silane coupling agent. The reason why the pigment particles adhere more firmly to the fingerprint component is because the affinity of the pigment particles for calcium lactate and the fingerprint component increases. Because the pigment particles adhere more firmly to the fingerprint component, the fingerprint detection powder according to the present invention allows the line formed by the fingerprint component to be hardly damaged even on a smooth surface, for example, flat glass, compared to a fingerprint detection powder that contains no silane coupling agent. Because the line formed by the fingerprint component is hardly damaged, the fingerprint detection powder according to the present invention makes it possible to collect a clear fingerprint image.

The form in which calcium lactate is contained is not particularly limited in the fingerprint detection powder according to the present invention. For example, calcium lactate may be in the form of calcium lactate particles. In this case, the fingerprint detection powder according to an embodiment of the present invention is a mixture containing pigment particles and calcium lactate particles. Alternatively, calcium lactate may be a component of a coating formed on the surface of the pigment particles (in the description of the present invention, this coating is referred to as "surface layer"). Calcium lactate may be a kind of component of the pigment particles.

When calcium lactate is contained in the surface layer of the pigment particles, the thickness of the surface layer is not particularly limited. The specific form of the surface layer is not also particularly limited.

The calcium lactate according to the present invention may be calcium L-lactate or calcium D-lactate. The calcium lactate according to the present invention may be hydrate.

In the fingerprint detection powder according to the present invention, the weight % of calcium lactate is not particularly limited. However, the weight % of calcium lactate is desirably 1 wt % or more and 40 wt % or less.

The form in which the silane coupling agent is contained is not particularly limited in the fingerprint detection powder according to the present invention. For example, the silane coupling agent may be a component of a coating formed on the surface of the pigment particles (in the description of the present invention, this coating is referred to as "surface layer"). The silane coupling agent may be dehydrated and condensed with hydroxyl groups on the surface of the pigment particles to form covalent bond.

When the silane coupling agent is contained in the surface layer of the pigment particles, the thickness of the surface layer is not particularly limited. The specific form of the surface layer is not also particularly limited.

The composition of the coupling agent is not particularly limited, as long as it is an organosilicon compound that binds an organic material to an inorganic material. Examples of the coupling agent are substances containing an organosilicon compound having a functional group that binds to an organic material and a functional group that binds to an inorganic material. In such substances, there are no particular limitations on the types of the functional group that binds to an organic material and the functional group that binds to an inorganic material. Examples of the functional group that binds to an organic material are an alkyl group, alkylene group, aryl group, vinyl group, amino group and thiol group. Examples of the alkyl group are a methyl group, ethyl group, propyl group, butyl group, pentyl group, hexyl group, heptyl group, octyl group, nonyl group, decyl group and icosyl group. Examples of the alkylene group are a methylene group, ethylene group, n-propylene group, n-butylene group, n-hexylene group, n-heptylene group, n-octylene group and n-dodecylene group. Examples of the aryl group are a phenyl group, benzyl group and tolyl group. Examples of the functional group that binds to an inorganic material are an alkoxy group. Examples of the alkoxy group are a methoxy group and ethoxy group.

The silane coupling agent according to the present invention preferably contains a substance represented by the following formula (1).

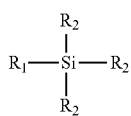

[Chemical Formula 2]

wherein $R_1$ is an alkyl group or an aryl group, and $R_2$ is an alkoxy group having 1 or 2 carbon atoms.

In the substance represented by the formula (1), $R_1$ is preferably an alkyl group having 7 or more and 10 or less carbon atoms. More preferably, the alkyl group is an octyl group. Examples of such a substance are n-octyltriethoxysilane. Examples of the substance in which $R_1$ is an alkyl group having 7 or more and 10 or less carbon atoms but the alkyl group is not an octyl group are n-decyltrimethoxysilane.

In the substance represented by the formula (1), examples of the substance in which $R_1$ is an alkyl group but is not an alkyl group having 7 or more and 10 or less carbon atoms are methyltrimethoxysilane. In the substances represented by the formula (1), examples of the substance in which $R_1$ is an aryl group are phenyltrimethoxysilane.

Among the organosilicon compounds having a functional group that binds to an organic material and a functional group that binds to an inorganic material, examples of substances not represented by the formula (1) are vinyl silane, epoxy silane, methacryl silane, acrylic silane, amino silane, mercapto silane and silazane. Among the organosilicon compounds having a functional group that binds to an organic material and a functional group that binds to an inorganic material, the vinyl silane refers to an organosilicon compound having a vinyl group as a functional group that binds to an organic material. Examples of the vinyl silane are vinyl trimethoxy silane and vinyl triethoxy silane. Among the organosilicon compounds having a functional group that binds to an organic material and a functional group that binds to an inorganic material, the epoxy silane refers to an organosilicon compound having an epoxy group as a functional group that binds to an organic material. Examples of the epoxy silane are 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane and 3-glycidoxypropyltriethoxysilane. Among the organosilicon compounds having a functional group that binds to an organic material and a functional group that binds to an inorganic material, the methacrylic silane refers to an organosilicon compound having a methacrylic group as a functional group that binds to an organic material. Examples of the methacrylic silane are 3-methacryloxypropylmethyldimethoxysilane, 3-methacryloxypropyltrimethoxysilane, 3-methacryloxypropylmethyldiethoxysilane and 3-methacryloxypropyltriethoxysilane. Among the organosilicon compounds having a functional group that binds to an organic material and a functional group that binds to an inorganic material, the acrylic silane refers to an organosilicon compound having an acrylic group as a functional group that binds to an organic material. Examples of the acrylic silane are 3-acryloxypropyltrimethoxysilane. Among the organosilicon compounds having a functional group that binds to an organic material and a functional group that binds to an inorganic material, the amino silane refers to an organosilicon compound having an amino group as a functional group that binds to an organic material. Examples of the amino silane are hydrochlorides of N-2-(aminoethyl)-3-aminopropylmethyldimethoxysilane, N-2-(aminoethyl)-3-aminopropylaminopropyltrimethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane and N-(vinylbenzyl)-2-aminoethyl-3-aminopropyltrimethoxysilane. Among the organosilicon compounds having a functional group that binds to an organic material and a functional group that binds to an inorganic material, the mercapto silane refers to an organosilicon compound having a thiol group as a functional group that binds to an organic material. Examples of the mercaptosilane are 3-mercaptopropylmethyldimethoxysilane and 3-mercaptopropyltrimethoxysilane. Among the silane coupling agents, the silazane refers to an organosilicon compound having a silicon-nitrogen bond. Examples of the silazane are 1,1,1,3,3,3-hexamethyldisilazane.

In the fingerprint detection powder according to the present invention, the weight % of silane coupling agent is not particularly limited. However, when the silane coupling agent includes an organosilicon compound having a functional group that binds to an organic material and a functional group that binds to an inorganic material, the weight % of the organosilicon compound is preferably 0.1 wt % or more and 20 wt % or less. The weight % of the organosilicon compound is more preferably 0.5 wt % or more and 5 wt % or less. When the weight % of the organosilicon compound is 0.5% or more, a remarkable improvement in detection ability is observed for a sample with less adhesion of fingerprint component. When the weight % of the organosilicon compound is 5 wt % or less, "smearing" and "fogging" in the ridges are suppressed. As a result, the detected fingerprint becomes clear.

In the fingerprint detection powder according to the present invention, specific components of the pigment particles are not particularly limited. Examples of substances well-known as pigments among components of the pigment particles are titanium oxide, aluminum oxide, zinc oxide, zirconium oxide, red iron oxide, yellow iron oxide, black iron oxide, silica, carbon black, aluminum powder and copper powder. Among them, titanium oxide is preferable as a component of pigment particles.

[Method for Producing Fingerprint Detection Powder]

A method for producing the fingerprint detection powder according to the present invention is not particularly limited. For example, the fingerprint detection powder according to the present invention may be produced by the method described below. When the fingerprint detection powder according to the present invention is produced by this method, first, an operator forms the pigment particles by a well-known method. The operator then mixes the pigment particles with the silane coupling agent. The operator then heats the mixture of the pigment particles and the silane coupling agent. The operator then places the heated mixture in a calcium lactate solution. The operator then removes the solvent from the calcium lactate solution. The residue after removal of the solvent is the fingerprint detection powder according to an embodiment of the present invention.

[Method for Using Fingerprint Detection Powder]

A method for using the fingerprint detection powder according to the present invention is the same as those for well-known fingerprint detection powders. Accordingly, a detailed description of the method will not be repeated.

EXAMPLES

Hereinafter, a description is made of Examples 1 to 27 according to one embodiment of the present invention together with Comparative Examples 1 to 4.

Example 1

An operator added a mixed solution of 2 g of n-octyltriethoxysilane (Z-6341 manufactured by Dow Corning Toray Co., Ltd.) and 2 g of methanol to 99 g of titanium oxide (CR-EL manufactured by Ishihara Sangyo Kaisha, Ltd.). The operator mixed them well for 5 minutes. The operator dried the mixture by heating at 120° C. for 2 hours. As a result, titanium oxide surface-modified with n-octyltriethoxysilane was obtained. The operator then dissolved 1 g of calcium L-lactate pentahydrate in 200 g of methanol. This was the calcium lactate solution. The operator added 99 g of titanium oxide surface-modified with n-octyltriethoxysilane to the calcium lactate solution. The operator stirred the calcium lactate solution for 30 minutes, and then dried the calcium lactate solution by heating at 70° C. This led to removal of the solvent. The resultant is a fingerprint detection powder according to this Example. The fingerprint detection powder according to this Example was titanium oxide particles provided with a surface layer containing n-octyltriethoxysilane and calcium L-lactate pentahydrate. In this case, the sum of n-octyltriethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of n-octyltriethoxysilane is 1.9%.

Example 2

The operator obtained a fingerprint detection powder according to this Example through the same procedure as in Example 1 except the following point. The point is that 2 g of methyltrimethoxysilane (Z-6366 manufactured by Dow Corning Toray Co., Ltd.) was used instead of 2 g of n-octyltriethoxysilane. In this case, the sum of methyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of methyltrimethoxysilane is 1.9%.

Example 3

The operator obtained a fingerprint detection powder according to this Example through the same procedure as in Example 1 except the following point. The point is that 2 g of n-decyltrimethoxysilane (Z-6210 manufactured by Dow Corning Toray Co., Ltd.) was used instead of 2 g of n-octyltriethoxysilane. In this case, the sum of n-decyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of n-decyltrimethoxysilane is 1.9%.

Example 4

The operator obtained a fingerprint detection powder according to this Example through the same procedure as in Example 1 except the following point. The point is that 2 g of phenyltrimethoxysilane (Z-6124 manufactured by Dow Corning Toray Co., Ltd.) was used instead of 2 g of n-octyltriethoxysilane. In this case, the sum of phenyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of phenyltrimethoxysilane is 1.9%.

Example 5

The operator obtained a fingerprint detection powder according to this Example through the same procedure as in Example 1 except the following point. The point is that 2 g of 3-aminopropyltrimethoxysilane (KBM-903 manufactured by Shin-Etsu Chemical Co., Ltd.) was used instead of 2 g of n-octyltriethoxysilane. In this case, the sum of 3-aminopropyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of 3-aminopropyltrimethoxysilane is 1.9%.

Example 6

The operator obtained a fingerprint detection powder according to this Example through the same procedure as in Example 1 except the following point. The point is that 2 g of 3-glycidoxypropyltrimethoxysilane (KBM-403 manufactured by Shin-Etsu Chemical Co., Ltd.) was used instead of 2 g of n-octyltriethoxysilane. In this case, the sum of 3-glycidoxypropyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of 3-glycidoxypropyltrimethoxysilane is 1.9%.

Example 7

The operator obtained a fingerprint detection powder according to this Example through the same procedure as in Example 1 except the following point. The point is that 2 g of vinyltrimethoxysilane (KBM-1003 manufactured by Shin-Etsu Chemical Co., Ltd.) was used instead of 2 g of n-octyltriethoxysilane. In this case, the sum of vinyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of vinyltrimethoxysilane is 1.9%.

Example 8

The operator obtained a fingerprint detection powder according to this Example through the same procedure as in Example 1 except the following point. The point is that 2 g of 3-methacryloxypropyltrimethoxysilane (Z-6030 manufactured by Dow Corning Toray Co., Ltd.) was used instead of 2 g of n-octyltriethoxysilane. In this case, the sum of 3-methacryloxypropyltrimethoxysilane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of 3-methacryloxypropyltrimethoxysilane is 1.9%.

Example 9

The operator obtained a fingerprint detection powder according to this Example through the same procedure as in Example 1 except the following point. The point is that 2 g of 1,1,1,3,3,3-hexamethyldisilazane (Z-6079 manufactured by Dow Corning Toray Co., Ltd.) was used instead of 2 g of n-octyltriethoxysilane. In this case, the sum of 1,1,1,3,3,3-hexamethyldisilazane (2 g), titanium oxide (99 g) and calcium L-lactate pentahydrate (1 g) is 102 g. The sum thereof is the weight of the fingerprint detection powder according to this Example. The weight of the fingerprint detection powder according to this Example is 102 g, so that the weight % of 1,1,1,3,3,3-hexamethyldisilazane is 1.9%.

Example 10

The operator obtained a fingerprint detection powder according to this Example through the same procedure as in Example 1 except the following point. The point is that the used amount of n-octyltriethoxysilane was 0.1 g. In this case, the sum of n-octyltriethoxysilane (0.1 g), titanium oxide (99 g) and calcium L-lactate pentahydrate (1 g) is 100.1 g. The sum thereof is the weight of the fingerprint detection powder according to this Example. The weight of the fingerprint detection powder according to this Example is 100.1 g, so that the weight % of n-octyltriethoxysilane is 0.1%.

Example 11

The operator obtained a fingerprint detection powder according to this Example through the same procedure as in Example 1 except the following point. The point is that the used amount of n-octyltriethoxysilane was 0.5 g. In this case, the sum of n-octyltriethoxysilane (0.5 g), titanium oxide (99 g) and calcium L-lactate pentahydrate (1 g) is 100.5 g. The sum thereof is the weight of the fingerprint detection powder according to this Example. The weight of the fingerprint detection powder according to this Example is 100.5 g, so that the weight % of n-octyltriethoxysilane is 0.5%.

Example 12

The operator obtained a fingerprint detection powder according to this Example through the same procedure as in Example 1 except the following point. The point is that the used amount of n-octyltriethoxysilane was 1 g. In this case, the sum of n-octyltriethoxysilane (1 g), titanium oxide (99 g) and calcium L-lactate pentahydrate (1 g) is 101 g. The sum thereof is the weight of the fingerprint detection powder according to this Example. The weight of the fingerprint detection powder according to this Example is 101 g, so that the weight % of n-octyltriethoxysilane is 1.0%.

Example 13

The operator obtained a fingerprint detection powder according to this Example through the same procedure as in Example 1 except the following point. The point is that the used amount of n-octyltriethoxysilane was 5 g. In this case, the sum of n-octyltriethoxysilane (5 g), titanium oxide (99 g) and calcium L-lactate pentahydrate (1 g) is 105 g. The sum thereof is the weight of the fingerprint detection powder according to this Example. The weight of the fingerprint detection powder according to this Example is 105 g, so that the weight % of n-octyltriethoxysilane is 4.8%.

Example 14

The operator obtained a fingerprint detection powder according to this Example through the same procedure as in Example 1 except the following point. The point is that the used amount of n-octyltriethoxysilane was 10 g. In this case, the sum of n-octyltriethoxysilane (10 g), titanium oxide (99 g) and calcium L-lactate pentahydrate (1 g) is 110 g. The sum thereof is the weight of the fingerprint detection powder according to this Example. The weight of the fingerprint detection powder according to this Example is 110 g, so that the weight % of n-octyltriethoxysilane is 9.1%.

Example 15

The operator obtained a fingerprint detection powder according to this Example through the same procedure as in Example 1 except the following point. The point is that the used amount of n-octyltriethoxysilane was 20 g. In this case, the sum of n-octyltriethoxysilane (20 g), titanium oxide (99 g) and calcium L-lactate pentahydrate (1 g) is 120 g. The sum thereof is the weight of the fingerprint detection powder according to this Example. The weight of the fingerprint detection powder according to this Example is 120 g, so that the weight % of n-octyltriethoxysilane is 16.7%.

Example 16

The operator obtained a fingerprint detection powder according to this Example through the same procedure as in Example 2 except the following point. The point is that the used amount of methyltrimethoxysilane was 0.1 g. In this case, the sum of methyltrimethoxysilane (0.1 g), titanium oxide (99 g) and calcium L-lactate pentahydrate (1 g) is 100.1 g. The sum thereof is the weight of the fingerprint detection powder according to this Example. The weight of the fingerprint detection powder according to this Example is 100.1 g, so that the weight % of methyltrimethoxysilane is 0.1%.

Example 17

The operator obtained a fingerprint detection powder according to this Example through the same procedure as in Example 2 except the following point. The point is that the used amount of methyltrimethoxysilane was 0.5 g. In this case, the sum of methyltrimethoxysilane (0.5 g), titanium oxide (99 g) and calcium L-lactate pentahydrate (1 g) is 100.5 g. The sum thereof is the weight of the fingerprint detection powder according to this Example. The weight of the fingerprint detection powder according to this Example is 100.5 g, so that the weight % of methyltrimethoxysilane is 0.5%.

Example 18

The operator obtained a fingerprint detection powder according to this Example through the same procedure as in Example 2 except the following point. The point is that the used amount of methyltrimethoxysilane was 1 g. In this case, the sum of methyltrimethoxysilane (1 g), titanium oxide (99 g) and calcium L-lactate pentahydrate (1 g) is 101 g. The sum thereof is the weight of the fingerprint detection powder according to this Example. The weight of the fingerprint detection powder according to this Example is 101 g, so that the weight % of methyltrimethoxysilane is 1.0%.

Example 19

The operator obtained a fingerprint detection powder according to this Example through the same procedure as in Example 2 except the following point. The point is that the used amount of methyltrimethoxysilane was 5 g. In this case, the sum of methyltrimethoxysilane (5 g), titanium oxide (99 g) and calcium L-lactate pentahydrate (1 g) is 105 g. The sum thereof is the weight of the fingerprint detection powder according to this Example. The weight of the fingerprint detection powder according to this Example is 105 g, so that the weight % of methyltrimethoxysilane is 4.8%.

Example 20

The operator obtained a fingerprint detection powder according to this Example through the same procedure as in Example 2 except the following point. The point is that the used amount of methyltrimethoxysilane was 10 g. In this case, the sum of methyltrimethoxysilane (10 g), titanium oxide (99 g) and calcium L-lactate pentahydrate (1 g) is 110 g. The sum thereof is the weight of the fingerprint detection powder according to this Example. The weight of the fingerprint detection powder according to this Example is 110 g, so that the weight % of methyltrimethoxysilane is 9.1%.

Example 21

The operator obtained a fingerprint detection powder according to this Example through the same procedure as in Example 2 except the following point. The point is that the used amount of methyltrimethoxysilane was 20 g. In this case, the sum of methyltrimethoxysilane (20 g), titanium oxide (99 g) and calcium L-lactate pentahydrate (1 g) is 120 g. The sum thereof is the weight of the fingerprint detection powder according to this Example. The weight of the fingerprint detection powder according to this Example is 120 g, so that the weight % of methyltrimethoxysilane is 16.7%.

Example 22

The operator obtained a fingerprint detection powder according to this Example through the same procedure as in Example 3 except the following point. The point is that the used amount of n-decyltrimethoxysilane was 0.1 g. In this case, the sum of n-decyltrimethoxysilane (0.1 g), titanium oxide (99 g) and calcium L-lactate pentahydrate (1 g) is 100.1 g. The sum thereof is the weight of the fingerprint detection powder according to this Example. The weight of the fingerprint detection powder according to this Example is 100.1 g, so that the weight % of n-decyltrimethoxysilane is 0.1%.

Example 23

The operator obtained a fingerprint detection powder according to this Example through the same procedure as in Example 3 except the following point. The point is that the used amount of n-decyltrimethoxysilane was 0.5 g. In this case, the sum of n-decyltrimethoxysilane (0.5 g), titanium oxide (99 g) and calcium L-lactate pentahydrate (1 g) is 100.5 g. The sum thereof is the weight of the fingerprint detection powder according to this Example. The weight of the fingerprint detection powder according to this Example is 100.5 g, so that the weight % of n-decyltrimethoxysilane is 0.5%.

Example 24

The operator obtained a fingerprint detection powder according to this Example through the same procedure as in Example 3 except the following point. The point is that the used amount of n-decyltrimethoxysilane was 1 g. In this case, the sum of n-decyltrimethoxysilane (1 g), titanium oxide (99 g) and calcium L-lactate pentahydrate (1 g) is 101 g. The sum thereof is the weight of the fingerprint detection powder according to this Example. The weight of the fingerprint detection powder according to this Example is 101 g, so that the weight % of n-decyltrimethoxysilane is 1.0%.

Example 25

The operator obtained a fingerprint detection powder according to this Example through the same procedure as in Example 3 except the following point. The point is that the used amount of n-decyltrimethoxysilane was 5 g. In this case, the sum of n-decyltrimethoxysilane (5 g), titanium oxide (99 g) and calcium L-lactate pentahydrate (1 g) is 105 g. The sum thereof is the weight of the fingerprint detection powder according to this Example. The weight of the fingerprint detection powder according to this Example is 105 g, so that the weight % of n-decyltrimethoxysilane is 4.8%.

Example 26

The operator obtained a fingerprint detection powder according to this Example through the same procedure as in Example 3 except the following point. The point is that the used amount of n-decyltrimethoxysilane was 10 g. In this case, the sum of n-decyltrimethoxysilane (10 g), titanium oxide (99 g) and calcium L-lactate pentahydrate (1 g) is 110 g. The sum thereof is the weight of the fingerprint detection powder according to this Example. The weight of the fingerprint detection powder according to this Example is 110 g, so that the weight % of n-decyltrimethoxysilane is 9.1%.

Example 27

The operator obtained a fingerprint detection powder according to this Example through the same procedure as in Example 3 except the following point. The point is that the used amount of n-decyltrimethoxysilane was 20 g. In this case, the sum of n-decyltrimethoxysilane (20 g), titanium oxide (99 g) and calcium L-lactate pentahydrate (1 g) is 120 g. The sum thereof is the weight of the fingerprint detection powder according to this Example. The weight of the fingerprint detection powder according to this Example is 120 g, so that the weight % of n-decyltrimethoxysilane is 16.7%.

Comparative Example 1

The operator dissolved 1 g of calcium L-lactate pentahydrate in 200 g of methanol. The resultant is a calcium lactate solution according to this Comparative Example. The operator added 99 g of titanium oxide (CR-EL manufactured by Ishihara Sangyo Kaisha, Ltd.) to the calcium lactate solution. The operator stirred the calcium lactate solution for 30 minutes. The operator then dried the calcium lactate solution by heating at 70° C. This heat drying led to removal of the solvent from the calcium lactate solution. The powder obtained by this heat drying is a fingerprint detection powder according to this Comparative Example.

Comparative Example 2

A fingerprint detection powder according to this Comparative Example is a commercially available titanium oxide powder (CR-EL manufactured by Ishihara Sangyo Kaisha, Ltd.).

Comparative Example 3

The operator mixed 2 g of n-octyltriethoxysilane (Z-6341 manufactured by Dow Corning Toray Co., Ltd.) and 2 g of methanol. The operator added the mixed solution obtained by the mixing to 99 g of titanium oxide. The operator mixed the mixture well for 5 minutes. The operator dried the mixture by heating at 120° C. for 2 hours. This led to removal of the solvent. The resultant is a fingerprint detection powder according to this Comparative Example. In this case, the sum of n-octyltriethoxysilane (2 g) and titanium oxide (99 g) is 101 g. The sum thereof is the weight of the fingerprint detection powder according to this Comparative Example. The weight of the fingerprint detection powder according to this Comparative Example is 101 g, so that the weight % of n-octyltriethoxysilane is 2.0%.

Comparative Example 4

A fingerprint detection powder according to this Comparative Example is a commercially available aluminum powder (PS24A manufactured by Police Science Industry, Ltd.).

[Fingerprint Detection from Sample with Less Adhesion of Fingerprint Component]

The operator confirmed that a clear fingerprint could be detected from a sample with less adhesion of fingerprint component by the following procedure. First, the operator put fingerprints on 20 portions on an acrylic board continuously using the same finger. The operator numbered these fingerprints from No. 1 to No. 20 according to the order the fingerprints were put. In other words, the No. 1 fingerprint is from a sample with the highest level of adhesion of fingerprint component among the 20 samples. The No. 20 fingerprint is from a sample with the lowest level of adhesion of fingerprint component among the 20 samples. Next, the operator applied the fingerprint detection powder according to Example 1 to these 20 samples with a brush. Application was done with a brush. As a result, 20 samples to which the fingerprint detection powder according to Example 1 was applied were created. Next, the operator created 20 samples to which each of the fingerprint detection powders according to Examples 2 to 27 and Comparative Examples 1 to 4 was applied by the same procedure. After the samples associated with Examples 1 to 27 and Comparative Examples 1 to 4 were obtained, the operator evaluated the sharpness of the fingerprint image for each sample based on observation results for the sample. The evaluation results are shown in Tables 1 and 2. In Tables 1 and 2, the double circles indicate that there is no pigment adhesion among the ridges of the fingerprint, and the line representing the fingerprint is dense. In Tables 1 and 2, the single circles indicate that there is no pigment adhesion among the ridges of the fingerprint, but the line representing the fingerprint is thin. In Tables 1 and 2, the triangle marks indicate that the fingerprint is not clear because the line representing the ridge is fogged or there is powder adhesion among the ridges. In Tables 1 and 2, the cross marks indicate that most of the fingerprint cannot be confirmed.

TABLE 1

|  | Example | | | | | | | | | Comparative Example | | | |
| --- | --- | --- | --- | --- | --- | --- | --- | --- | --- | --- | --- | --- | --- |
|  | 1 | 2 | 3 | 4 | 5 | 6 | 7 | 8 | 9 | 1 | 2 | 3 | 4 |
| No. 1 | ⊙ | ⊙ | ⊙ | ⊙ | ⊙ | ○ | ⊙ | Δ | ⊙ | ⊙ | ○ | ⊙ | Δ |
| No. 5 | ⊙ | ⊙ | ⊙ | ⊙ | ○ | Δ | ○ | Δ | ⊙ | ○ | Δ | ⊙ | Δ |
| No. 10 | ⊙ | ⊙ | ⊙ | ○ | ○ | X | Δ | X | ○ | Δ | Δ | ○ | Δ |
| No. 15 | ⊙ | ○ | ⊙ | Δ | X | X | X | X | Δ | Δ | X | Δ | Δ |
| No. 20 | ⊙ | ○ | ○ | Δ | X | X | X | X | X | X | X | Δ | Δ |

TABLE 2

|  | Example | | | | | | | | | | | | | | | | | |
| --- | --- | --- | --- | --- | --- | --- | --- | --- | --- | --- | --- | --- | --- | --- | --- | --- | --- | --- |
|  | 10 | 11 | 12 | 13 | 14 | 15 | 16 | 17 | 18 | 19 | 20 | 21 | 22 | 23 | 24 | 25 | 26 | 27 |
| No. 1 | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ |
| No. 5 | ○ | ⊙ | ⊙ | ⊙ | ⊙ | ⊙ | ○ | ⊙ | ⊙ | ⊙ | ⊙ | ⊙ | ⊙ | ○ | ⊙ | ⊙ | ○ | Δ |
| No. 10 | ○ | ⊙ | ⊙ | ⊙ | ○ | ○ | ○ | ⊙ | ⊙ | ⊙ | Δ | Δ | ○ | Δ | ⊙ | ⊙ | ○ | Δ |
| No. 15 | Δ | ⊙ | ⊙ | ○ | Δ | Δ | Δ | Δ | ○ | Δ | X | X | X | Δ | ⊙ | ○ | Δ | X |
| No. 20 | Δ | ⊙ | ⊙ | Δ | Δ | Δ | Δ | Δ | Δ | X | X | X | X | Δ | ○ | Δ | Δ | X |

Figure 2:
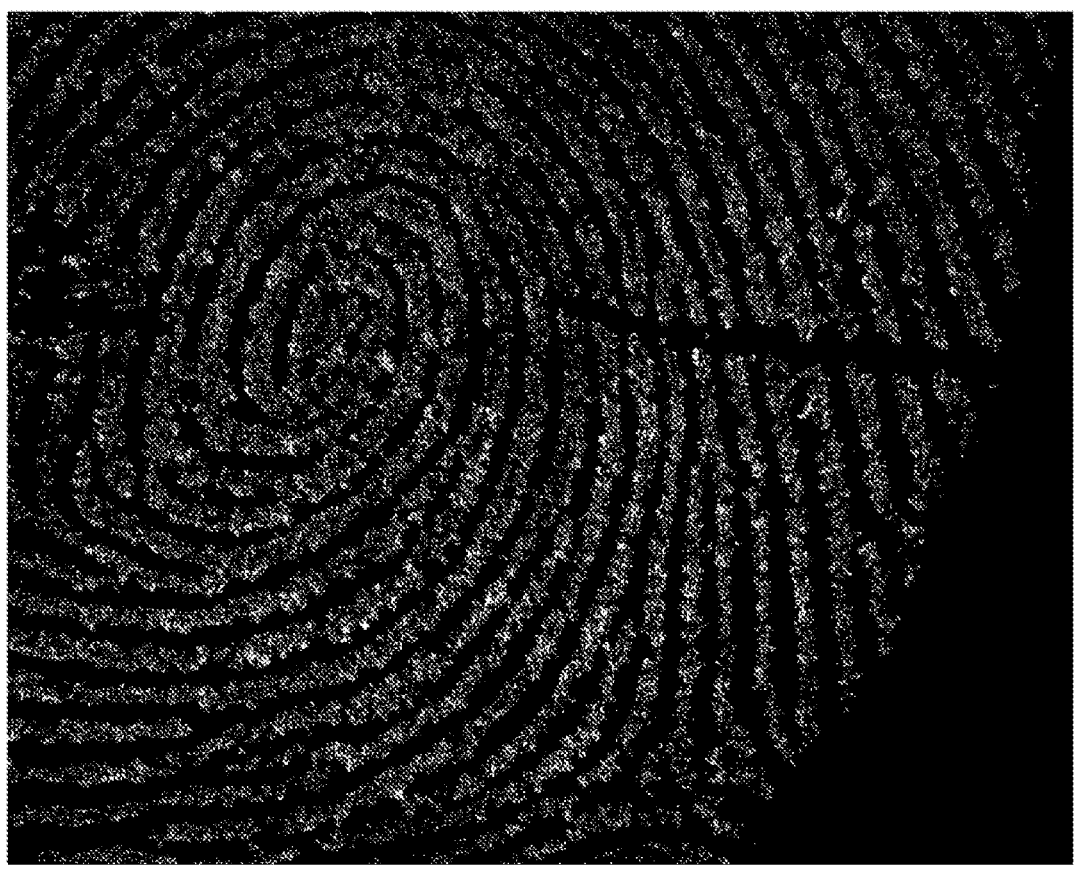
FIG. 2 is a fingerprint image when a fingerprint detection powder according to Example 1 is applied to the fingerprint No. 15 attached to an acrylic plate.
Figure 3:
FIG. 3 is a fingerprint image when a fingerprint detection powder according to Example 1 is applied to the fingerprint No. 20 attached to an acrylic plate.
Figure 4:
FIG. 4 is a fingerprint image when a fingerprint detection powder according to Comparative Example 1 is applied to the fingerprint No. 1 attached to an acrylic plate.
Figure 5:
FIG. 5 is a fingerprint image when a fingerprint detection powder according to Comparative Example 1 is applied to the fingerprint No. 15 attached to an acrylic plate.
Figure 6:
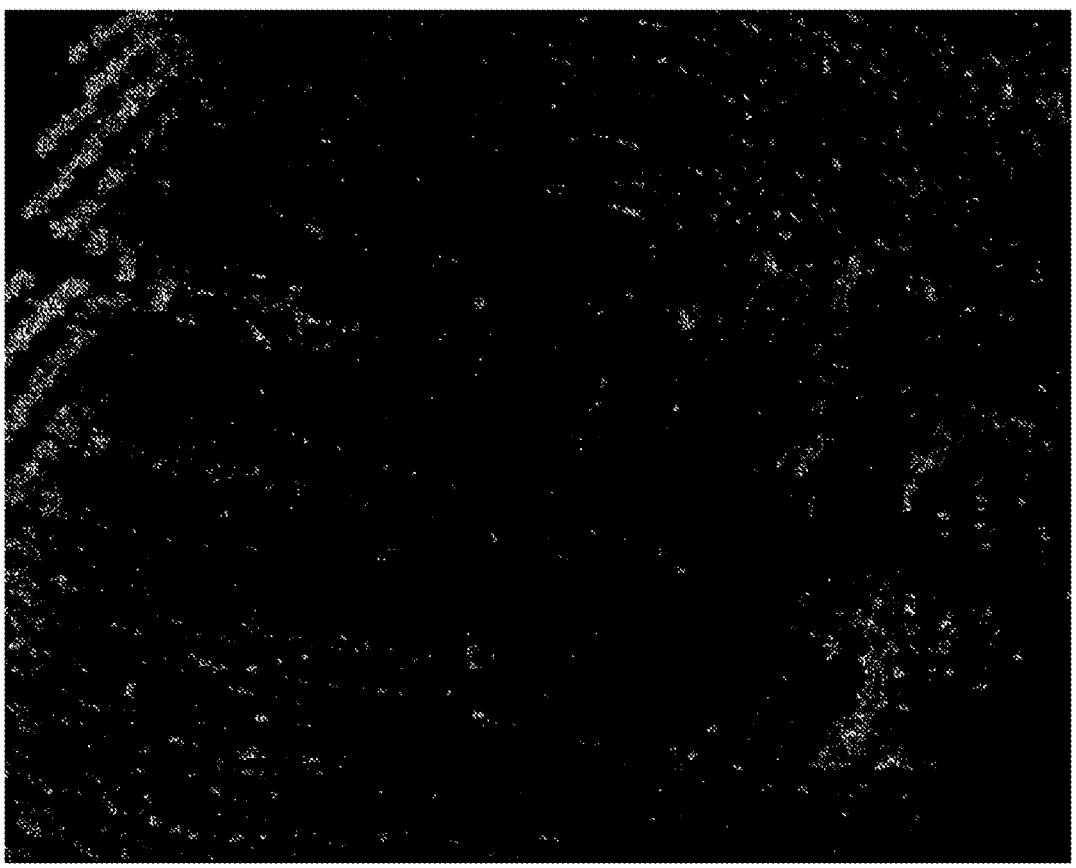
FIG. 6 is a fingerprint image when a fingerprint detection powder according to Comparative Example 1 is applied to the fingerprint No. 20 attached to an acrylic plate.
Figure 7:
FIG. 7 is a fingerprint image when a fingerprint detection powder according to Comparative Example 4 is applied to the fingerprint No. 1 attached to an acrylic plate.
Figure 8:
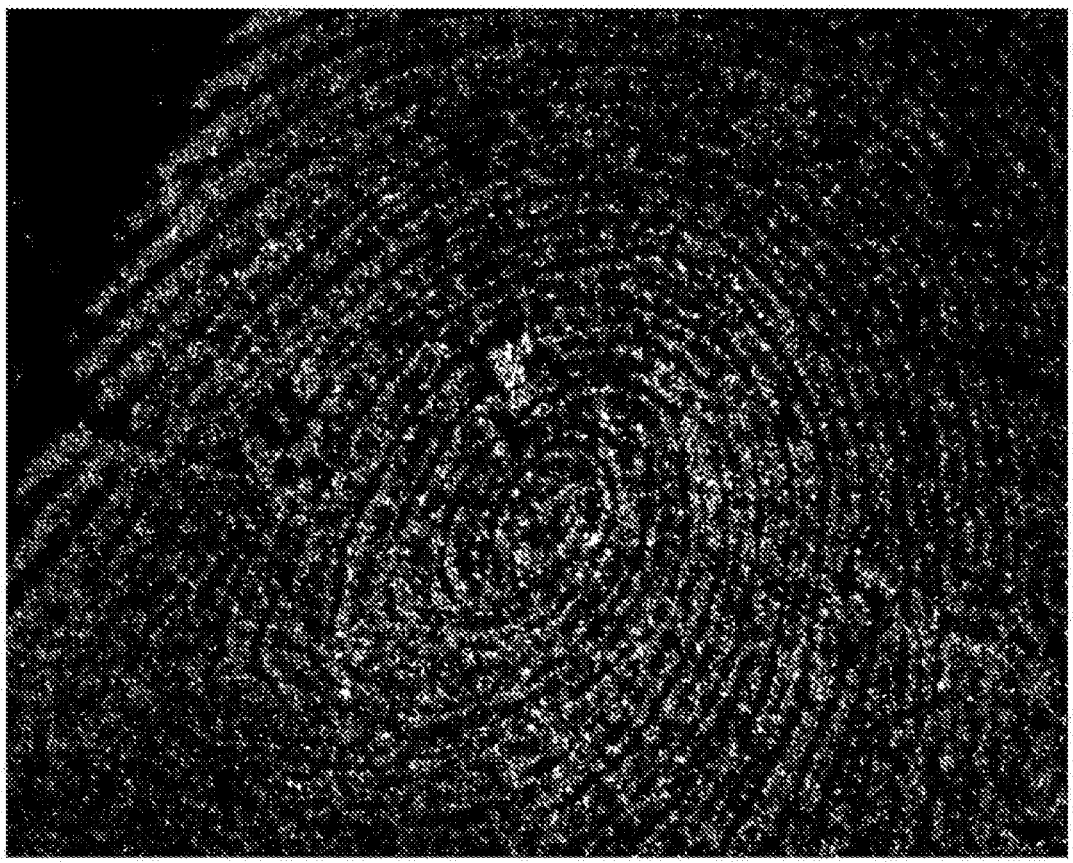
FIG. 8 is a fingerprint image when a fingerprint detection powder according to Comparative Example 4 is applied to the fingerprint No. 15 attached to an acrylic plate.
Figure 9:
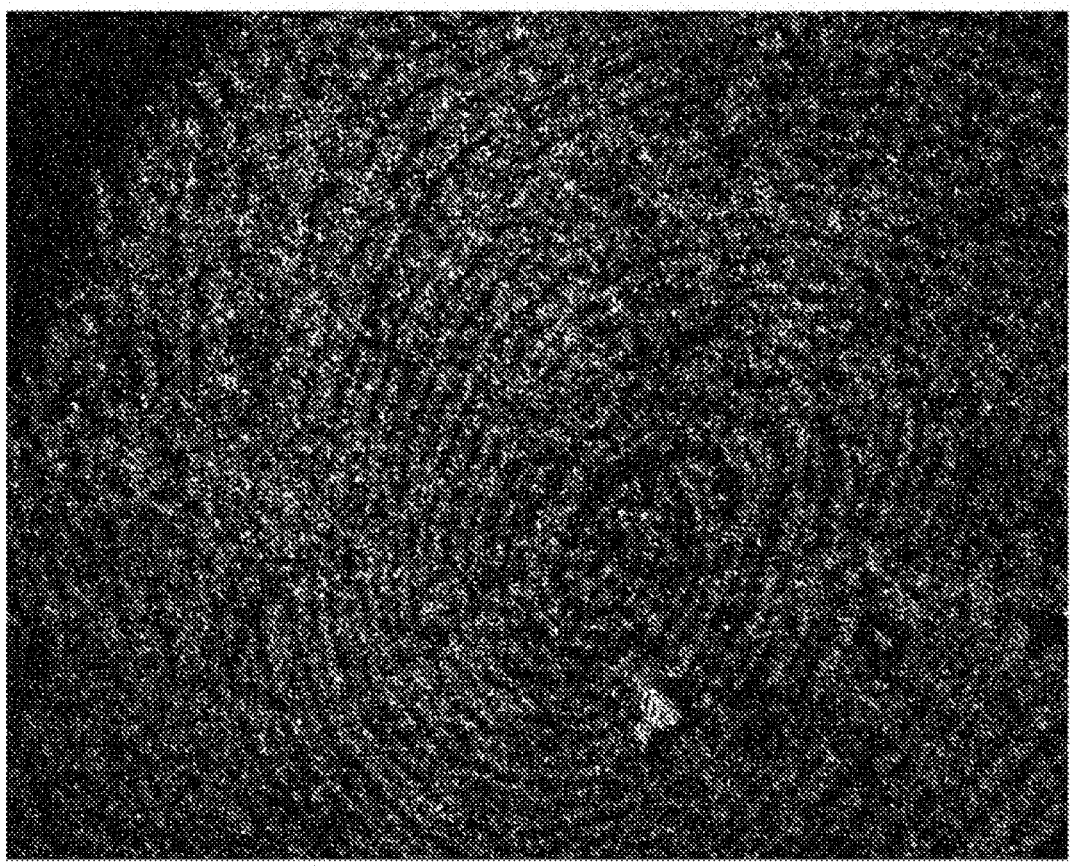
FIG. 9 is a fingerprint image when a fingerprint detection powder according to Comparative Example 4 is applied to the fingerprint No. 20 attached to an acrylic plate.

FIG. 1 is a fingerprint image when the fingerprint detection powder according to Example 1 is applied to the No. 1 fingerprint. FIG. 2 is a fingerprint image when the fingerprint detection powder according to Example 1 is applied to the No. 15 fingerprint. FIG. 3 is a fingerprint image when the fingerprint detection powder according to Example 1 is applied to the No. 20 fingerprint. FIG. 4 is a fingerprint image when the fingerprint detection powder according to Comparative Example 1 is applied to the No. 1 fingerprint. FIG. 5 is a fingerprint image when the fingerprint detection powder according to Comparative Example 1 is applied to the No. 15 fingerprint. FIG. 6 is a fingerprint image when the fingerprint detection powder according to Comparative Example 1 is applied to the No. 20 fingerprint. FIG. 7 is a fingerprint image when the fingerprint detection powder according to Comparative Example 4 is applied to the No. 1 fingerprint. FIG. 8 is a fingerprint image when the fingerprint detection powder according to Comparative Example 4 is applied to the No. 15 fingerprint. FIG. 9 is a fingerprint image when the fingerprint detection powder according to Comparative Example 4 is applied to the No. 20 fingerprint.

As to Examples 1 to 4, it was confirmed that a clear fingerprint image equivalent to or clearer than those by Comparative Examples 1 to 4 could be collected from a sample with less adhesion of fingerprint component. The fingerprint detection powder according to Comparative Example 1 allowed for clear fingerprint detection for a sample with high-level adhesion of fingerprint component, but as the fingerprint component became thinner, the ridges fogged or disappeared. The fingerprint detection powder according to Comparative Example 2 did not allow for clear fingerprint detection, because the detected fingerprint was thin, regardless of the level of adhesion of fingerprint component. When fingerprints were collected from samples with less adhesion of fingerprint component, the fingerprint detection powder according to Comparative Example 3 exhibited pigment adhesion outside the ridges, compared to the fingerprint detection powders according to Examples 1 to 4 and the fingerprint detection powder according to Comparative Example 1. This is presumably because the surface treatment with n-octyltriethoxysilane increases adhesion of the pigment to portions other than the fingerprint component. The fingerprint detection powder according to Comparative Example 4 allowed for fingerprint detection even from samples with less adhesion of fingerprint component, but the fingerprint image was unclear due to high-level adhesion of pigment to portions other than the ridges.

As to Examples 10 to 15, when the proportion of n-octyltriethoxysilane in the fingerprint detection powder was 0.5 wt % or more and 5 wt % or less, a remarkable improvement in fingerprint detection ability for samples with less adhesion of fingerprint component was observed. As to Examples 16 to 27, when the proportion of the coupling agent in the fingerprint detection powder was 1 wt % or more and 5 wt % or less, a remarkable improvement in fingerprint detection ability for samples with less adhesion of fingerprint components was observed.

From the above results, the fingerprint detection powder according to Examples 1 to 4 exhibited superior results in sharpness of the detected fingerprint, compared to the fingerprint detection powders according to Comparative Examples 1 to 4. In addition, the effects of the fingerprint detection powders according to Examples 1 to 4 are particularly remarkable when the proportion of the coupling agent in the powder is 0.5 wt % or more and 5 wt % or less. The fingerprint detection powder according to the present invention has a superior effect compared to conventional fingerprint detection powders in that a clear fingerprint can be detected for a sample with less adhesion of fingerprint component without damaging the ridges.

[Fingerprint Detection from Glassy Surface]

In order to show that it is possible to collect a clear fingerprint image even from a fingerprint attached to a smooth glassy surface, the sharpness of image when the fingerprint detection powder was applied to a fingerprint attached to a glass plate and a fingerprint attached to a tile plate was evaluated. The evaluation procedure is as follows. First, the operator put fingerprints on sample surfaces. Thereafter, the operator immediately applied the fingerprint detection powder to portions where the fingerprint was put. Application was done with a brush. Based on the observation results, the sharpness of the detected fingerprint for the sample on the glassy surface was evaluated. The evaluation results are shown in Tables 3 and 4. In Tables 3 and 4, the double circles indicate that the fingerprint clearly remains with respect to the application of the fingerprint detection powder. The single circles indicate that the ridge can be confirmed, but the line representing the fingerprint is thin. The triangle marks indicate that there is pigment adhesion among the ridges, and the fingerprint is unclear. The x marks indicate that the ridge is scraped.

TABLE 3

| | Example | | | | | | | | | Comparative Example | | | |
|---|---|---|---|---|---|---|---|---|---|---|---|---|---|
| | 1 | 2 | 3 | 4 | 5 | 6 | 7 | 8 | 9 | 1 | 2 | 3 | 4 |
| Glass | ⊙ | ○ | ⊙ | ○ | ○ | X | X | X | X | X | X | △ | △ |
| Tile | ⊙ | ⊙ | ⊙ | ○ | ○ | X | X | ○ | ○ | X | X | ○ | △ |

TABLE 4

| | Example | | | | | | | | | | | | | | | | | |
|---|---|---|---|---|---|---|---|---|---|---|---|---|---|---|---|---|---|---|
| | 10 | 11 | 12 | 13 | 14 | 15 | 16 | 17 | 18 | 19 | 20 | 21 | 22 | 23 | 24 | 25 | 26 | 27 |
| Glass | ○ | ⊙ | ⊙ | ⊙ | △ | △ | X | ○ | ⊙ | ○ | △ | X | X | ⊙ | ⊙ | ⊙ | ○ | X |
| Tile | ○ | ⊙ | ⊙ | ⊙ | ○ | ○ | X | ⊙ | ⊙ | ⊙ | ○ | ○ | ○ | ⊙ | ⊙ | ⊙ | ⊙ | ○ |

Figure 10:
FIG. 10 is a fingerprint image when a fingerprint detection powder according to Example 1 is applied to a glass plate attached with a fingerprint.
Figure 11:
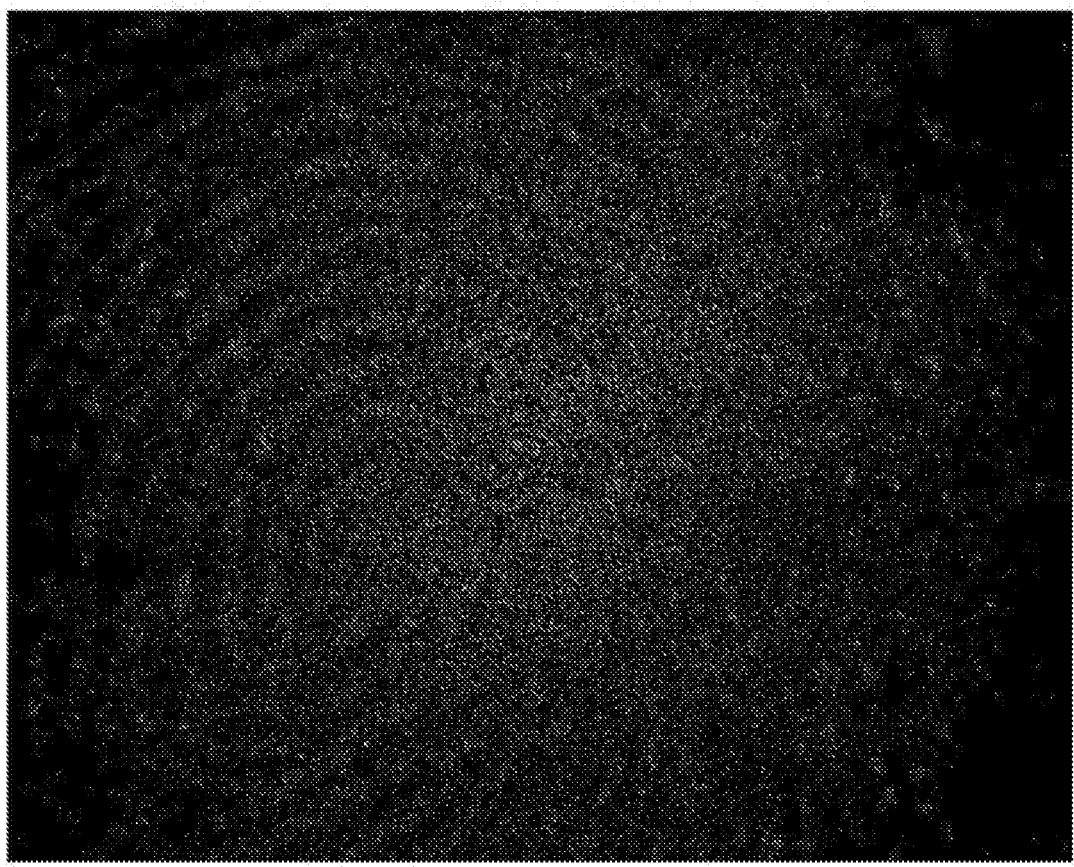
FIG. 11 is a fingerprint image when a fingerprint detection powder according to Comparative Example 1 is applied to a glass plate attached with a fingerprint.
Figure 12:
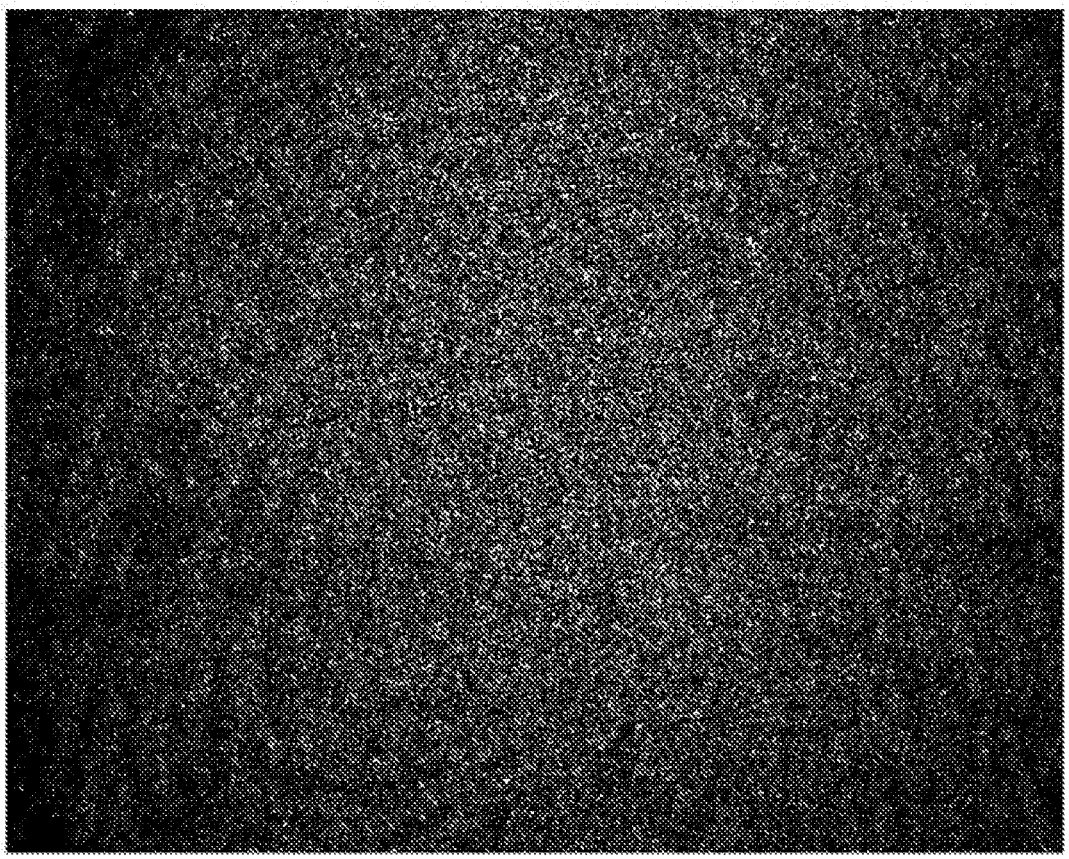
FIG. 12 is a fingerprint image when a fingerprint detection powder according to Comparative Example 4 is applied to a glass plate attached with a fingerprint.

FIG. 10 is a fingerprint image when the fingerprint detection powder according to Example 1 is applied to a fingerprint immediately after the fingerprint is put on a glass plate. FIG. 11 is a fingerprint image when the fingerprint detection powder according to Comparative Example 1 is applied to a fingerprint immediately after the fingerprint is put on a glass plate. FIG. 12 is a fingerprint image when the fingerprint detection powder according to Comparative Example 4 is applied to a glass plate attached with a fingerprint.

According to Tables 3 and 4, it is found that the fingerprint detection powder according to Example 1 and the fingerprint detection powder according to Example 3 are able to achieve fingerprint detection on a glassy surface without damaging the ridges. The fingerprint detection powder according to Example 2 was able to achieve clear detection of a fingerprint attached to the tile surface. However, the fingerprint detection powder according to Example 2 was not able to produce a darker development of a fingerprint on a glass surface with higher smoothness. The fingerprint detection powder according to Example 4 and the fingerprint detection powder according to Example 5 were able to achieve fingerprint detection on a glassy surface, but the color development was poor. The fingerprint detection powder according to Example 6 and the fingerprint detection powder according to Example 7 were not able to achieve fingerprint detection because the fingerprint component adhered to a glassy surface was peeled off by the application. The fingerprint detection powder according to Example 8 and the fingerprint detection powder according to Example 9 were able to achieve fingerprint detection on the tile, but the color development was poor. In addition, the fingerprint detection powder according to Example 8 and the fingerprint detection powder according to Example 9 were not able to achieve detection of a fingerprint attached to a glass surface with higher smoothness. This is because the ridges of the fingerprint were peeled off. The fingerprint detection powder according to Comparative Example 1 and the fingerprint detection powder according to Comparative Example 2 were not able to achieve fingerprint detection on a glassy surface. The fingerprint detection powder according to Comparative Example 3 and the fingerprint detection powder according to Comparative Example 4 were able to achieve fingerprint detection on a glassy surface. However, when the fingerprint detection powder according to Comparative Example 1 and the fingerprint detection powder according to Comparative Example 2 were used, the fingerprint image was unclear due to adhesion of the pigment outside the ridges.

As to the fingerprint detection powder according to Examples 10 to 27, when the proportion of the coupling agent in the fingerprint detection powder was 0.5 wt % or more and 5 wt % or less, a particularly remarkable improvement in fingerprint detection ability for a glassy surface was observed. Compared to a case where the proportion of the coupling agent in the fingerprint detection powder exceeded 10 wt %, the ridges were less likely to produce smearing and fogging, so that a clear fingerprint detection could be achieved.

Even when the proportion of the coupling agent in the fingerprint detection powder was 0.1 wt %, there was an improvement effect. However, the color development was more intense when the proportion of the coupling agent was 0.5 wt % or more and 5 wt % or less.

As mentioned above, the fingerprint detection powders according to Examples 1 to 3 were able to achieve detection of a clear fingerprint image even on a smooth glassy surface, compared to the fingerprint detection powders according to Comparative Examples 1 to 4. In addition, when the proportion of the coupling agent in the fingerprint detection powder is 0.5 wt % or more and 5 wt % or less, the effect is particularly remarkable.

INDUSTRIAL APPLICABILITY

The present invention can be used for a fingerprint detection powder for identification in criminal investigation agencies such as police.

The invention claimed is:

1. A fingerprint detection powder, comprising: pigment particles;
calcium lactate; and
silane coupling agent,
wherein the surface of the pigment particles is covered with the calcium lactate together the silane coupling agent.

2. The fingerprint detection powder according to claim 1, wherein the silane coupling agent comprises a substance represented by the following formula, (1)

[Chemical Formula 1]

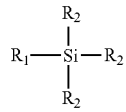

wherein $R_1$ is an alkyl group or an aryl group, and $R_2$ is an alkoxy group having 1 or 2 carbon atoms.

3. The fingerprint detection powder according to claim 2, wherein $R_1$ is an alkyl group having 7 or more and 10 or less carbon atoms.

4. The fingerprint detection powder according to claim 3, wherein the alkyl group having 7 or more and 10 or less carbon atoms is an octyl group.

5. The fingerprint detection powder according to claim 4, Wherein a weight % of the substance represented by the formula (1) in the fingerprint detection powder is 0.1 wt % or more and 20 wt % or less.

6. The fingerprint detection powder according to claim 4, wherein a weight % of the substance represented by the formula (1) in the fingerprint detection powder is 0.5 wt % or more and 5 wt % or less.

7. The fingerprint detection powder according to claim wherein the calcium lactate is calcium L-lactate.

8. The fingerprint detection powder according to claim 7, wherein the calcium L-lactate is hydrate.

9. The fingerprint detection powder according to claim 1, wherein the pigment particles comprise at least one selected from the group consisting of titanium oxide, aluminum oxide, zinc oxide, zirconium oxide, red iron oxide, yellow iron oxide, black iron oxide, silica, carbon black, aluminum powder and copper powder.

10. The fingerprint detection powder according to claim 1, Wherein a weight % of the substance represented by the formula (1) in the fingerprint detection powder is 0.5 wt % or more and 5 wt % or less.

* * * * *